(12) United States Patent
Bucala et al.

(10) Patent No.: US 6,420,188 B1
(45) Date of Patent: Jul. 16, 2002

(54) SCREENING ASSAY FOR THE IDENTIFICATION OF INHIBITORS FOR MACROPHAGE MIGRATION INHIBITORY FACTOR

(75) Inventors: Richard Bucala, New York, NY (US); Peter C. Ulrich, Old Tappan, NJ (US); Xini Xhang, Jericho; Anthony Cerami, Shelter Island, both of NY (US)

(73) Assignee: The Picower Institute for Medical Research, Manhasset, NY (US)

( * ) Notice: Subject to any disclaimer, the term of this patent is extended or adjusted under 35 U.S.C. 154(b) by 0 days.

(21) Appl. No.: 08/602,929

(22) Filed: Feb. 16, 1996

(51) Int. Cl.[7] ........................ G01N 33/53; C07D 307/50
(52) U.S. Cl. ........................ 436/500; 435/7.1; 549/490; 549/491
(58) Field of Search ............................. 514/12; 549/490, 549/491; 424/1.29; 435/7.1; 436/500

(56) References Cited

U.S. PATENT DOCUMENTS 5,384,116 A * 1/1995 Pawelek et al. ............... 424/63

OTHER PUBLICATIONS

Rosengren et al., Molecular Medicine., vol. 2., No. 1, pp. 143–149, Jan. 1996.*
Calandra, et al., "MIF as a Glucocorticoid–Induce Modulator of Cytokine Production", Nature, vol. 377, pp. 68–71 (Sep. 1995).
Bernhagen, et al., "Purification, Bioactivity, and Secondary Structure Analysis of Mouse and Human Macrophage Migration Inhibitory Factor (MIF)", Biochemistry, vol. 33, pp. 14144–14155 (1994).
Calandra, et al., "The Macrophage is an Important and Previously Unrecognized Source of Macrophage Migration Inhibitory Factors", J Exp Med (The Rockefeller University Press), vol. 179, pp. 1895–1902 (Jun. 1994).
Bernhagen, et al., "MIF is a Pituitary–Derived Cytokine that Potentiates Lethal Endotoxaemia", Nature, vol. 365, pp. 756–759 (Oct. 1993).
Wistow, et al., "A Macrophage Migration Inhibitory Factor is Expressed in the Differentiating Cells of the Eye Lens", Proc Natl Acad Sci USA, vol. 90, pp. 1272–1275 (Feb. 1993).
Aroca, et al., "Regulation of the Final Phase of Mammalian Melanogenesis", Eur J Biochem, vol. 208, pp. 155–163 (1992).
Bucala, et al., "Advanced Glycosylation: Chemistry, Biology, and Implications for Diabetes and Aging", Advances in Pharmacology, vol. 23, pp. 1–34 (1992).
Weiser, et al., "Molecular Cloning of a cDNA Encoding a Human Macrophage Migration Inhibitory Factor", Proc Natl Acad Sci USA, vol. 86, pp. 7522–7526 (Oct. 1989).

* cited by examiner

Primary Examiner—Radmashri Ponnaluri
(74) Attorney, Agent, or Firm—Piper Rudnick LLP; Steven B. Kelber (57) ABSTRACT

The present invention encompasses assays to identify compounds that inhibit the enzymatic activity of MIF which catalyzes the tautomerization of MIF-substrates, such as D-dopachrome to DHICA. In general, the assay is conducted in vitro by adding, mixing or combining MIF and a suitable substrate in the presence or absence of a test compound, and measuring the tautomerization of the substrate. The test compounds that inhibit tautomerization in the assay are identified as MIF inhibitors.

3 Claims, 1 Drawing Sheet

FIG.1

SCREENING ASSAY FOR THE IDENTIFICATION OF INHIBITORS FOR MACROPHAGE MIGRATION INHIBITORY FACTOR

1. INTRODUCTION

The present invention relates to screening assays for the identification of inhibitors of the biological activity of macrophage migration inhibitory factor (MIF). In addition, the present invention relates to the organic molecules, proteins and peptides identified by the screening assay. In particular, the invention relates to the uses of such identified compounds in pharmacological compositions and methods for the treatment of various conditions involving cytokine-mediated toxicity, which include, but are not limited to shock, inflammation, graft-versus-host disease, and/or autoimmune diseases.

2. BACKGROUND OF THE INVENTION

Infection by a variety of microorganisms including not only bacteria but also viruses, fungi, and parasites can induce septic shock, a multifaceted pathological condition characterized most prominently by deleterious hemodynamic changes and coagulopathy leading to multiple organ failure and often to death. In fact, the shock syndrome is more properly associated with the host's response to invasion rather than just infection, as cancer and trauma, for instance, can also serve as initiators. In the case of infection by gram-negative bacteria, one of the best studied examples, it is believed that the appearance of bacterial endotoxins such as lipopolysaccharide (LPS) in the host bloodstream leads to the endogenous production of a variety of host factors that directly and indirectly mediate the toxicity of LPS, which itself is relatively innocuous for most cells. These host-derived mediators include many now well-recognized inflammatory cytokines and classical endocrine hormones in addition to a number of other endogenous factors such as leukotrienes and platelet activating factor. It is generally acknowledged, however, that the full cast of participants and each of their interrelated roles in the host response remains incompletely appreciated.

In general, those mediators that appear earlier in an invaded host are thought to trigger the release of later appearing factors. Also, many endogenous mediators not only exert direct effector functions at their target tissues, but also prime local and remote tissues for subsequent responses to other mediators. This interacting network of host factors has been termed the "cytokine cascade." This term is meant to indicate the rapid extension and amplification of the host response in such a way that only one or a few initiating stimuli trigger the eventual release and participation of scores of endogenous mediators. Although a number of features of the host response are thought to assist in fighting off invasion, an overly robust or poorly modulated host response can rapidly accelerate to produce such profound alterations in host homeostasis at the cellular, tissue, and systemic levels that death may ensue within hours.

2.1. The Pituitary as a Source of Protective Cytokines

Recent studies suggest that the pituitary gland may produce factors that inhibit the production of endotoxin-induced cytokines and other mediators of the host response, such as TNFα and IL-1, and thus may serve as a source for potentially protective factors that may be used to treat shock and/or other inflammatory responses. (Suzuki et al., 1986, Am. J. Physiol. 250: E470–E474; Sternberg et al., 1989, Proc. Natl. Acad. Sci. USA 86: 2374–2378; Zuckerman et al., 1989, Eur. J. Immunol. 19: 301–305; Edwards III et al., 1991, Endocrinol. 128: 989–996; Edwards III et al., 1991b, Proc. Natl. Acad. Sci. USA 88: 2274–2277, Silverstein et al., 1991, J. Exp. Med. 173:357–365). In these studies, hypophysectomized mice (i.e., animals that have had their pituitary glands surgically removed) exhibited a markedly increased sensitivity to LPS injection relative to sham-operated control mice. In fact, the LPS $LD_{100}$ for control mice was approximately 1–2 logs higher than that determined for the hypophysectomized mice, suggesting that the pituitary gland produces one or more factors that may act to increase the host animal's ability to resist endotoxin challenge. Some of these studies implicate the involvement of ACTH and adrenocorticosteroids (e.g., Edwards III et al., 1991a and 1991b, supra); however, other data suggest the existence of other protective factors derived from the pituitary.

Very recently, murine macrophage migration inhibitory factor (MIF) was identified as an LPS-induced pituitary protein (Bernhagen et al., 1993, J. Cell. Biochem. Supplement 17B, Abstract E306). While it was hypothesized that MIF was one of the pituitary protective factors capable of counteracting the adverse effects of cytokines in endotoxemias, it was found that MIF actually exacerbates endotoxin-induced shock, and that inhibition of MIF activity can be used to treat otherwise lethal effects of cytokine-mediated activity (see Application Ser. No. 08/243,342, which is incorporated by reference herein in its entirety). As explained in the subsection below, MIF has been re-defined recently to be an anterior pituitary hormone, a macrophage cytokine, and a critical component of the host response to septic shock (Bernhagen et al., 1993, Nature 365:756–759; Calandra et al., 1994, J. Exp. Med. 179:1895–1902; Calandra et al., 1995, Nature 377:68–71). MIF exists preformed in various cell types and in the last few years has been fortuitously identified in several other organ systems and physiological contexts.

2.2. MIF: Macrophage Migration Inhibitory Factor

Although MIF was first described over 30 years ago as a T cell product that inhibits the random migration of guinea pig macrophages in an in vitro assay (George & Vaughan, 1962, Proc. Soc. Exp. Biol. Med. 111:514–521; Bloom & Bennett, 1966, Science 158: 80–82; David, 1966, Proc. Natl. Acad. Sci. USA 65: 72–77), the precise role of MIF in either local or systemic inflammatory responses had remained largely undefined. MIF has been reported to be associated with delayed-type hypersensitivity reactions (Bloom & Bennett, 1966, supra; David, 1966, supra), to be produced by lectin-activated T-cells (Weiser et al., 1981, J. Immunol. 126: 1958–1962), and to enhance macrophage adherence, phagocytosis and tumoricidal activity (Nathan et al., 1973, J. Exp. Med. 137: 275–288; Nathan et al., 1971, J. Exp. Med. 133: 1356–1376; Churchill et al., 1975, J. Immunol. 115: 781–785). Unfortunately, many of these studies used mixed culture supernatants that were shown later to contain other cytokines such as IFN-γ and IL-4 that also have migration inhibitory activity (McInnes & Rennick, 1988, J. Exp. Med. 167: 598–611; Thurman et al., 1985, J. Immunol. 134: 305–309).

Recombinant human MIF was originally cloned from human T cells (Weiser et al., 1989, Proc. Natl. Acad. Sci. USA 86: 7522–7526), and although the biological activity profile of MIF is incompletely known and has been debated, MIF has been shown to activate blood-derived macrophages to kill intracellular parasites and tumor cells in vitro, to stimulate IL-1β and TNFα expression, and to induce nitric oxide synthesis (reviewed in Bernhagen et al., 1994, Biochemistry 33:14144–14155).

MIF has been described recently to be an anterior pituitary hormone and to be released from immune cells stimulated by low concentrations of glucocorticoids. Once secreted MIF acts to control, or counter-regulate, the immunosuppressive effects of glucocorticoids on inflammatory cytokine production and acts to modulate the potent anti-inflammatory properties of glucocorticoids which are necessarily produced as part of the host response to infection and tissue invasion (Calandra et al., 1995, Nature 377:68–71). MIF is a critical component of the immune system and acts to counter the immunosuppressive effect of glucocorticoids to regulate inflammation and immunity.

Despite the interest in MIF activity, the lack of any pharmacological inhibitors of MIF has continued to hinder the investigation of the precise biological role of this molecule. For example, in contrast to its expected function as a protective hypothalamus factor, MIF proved to exacerbate lethality in several models of septic shock, indicating that a robust MIF response within the cytokine cascade may be undesired in a number of clinical settings. Given the critical role that MIF plays in cytokine-mediated toxicity in the host immune response, it would be of interest to use inhibitors of MIF to treat various conditions involving cytokine-mediated toxicity, including shock, inflammation, graft versus host disease, and/or immune diseases. However, other than antibodies directed against the MIF protein, there are no known exogenous inhibitors of MIF immunologic activity. Furthermore, the lack of defined cellular and biochemical activities of MIF has made it very difficult for researchers to develop an assay to specifically measure and quantitate MIF immunologic activity and identify MIF inhibitors. The lack of an in vitro assay to identify MIF inhibitors has hampered the investigation of the precise biological profile of this molecule in the immune response and the development of a treatment for disorders related to cytokine-mediated toxicity.

3. SUMMARY OF THE INVENTION

The present invention relates to a rapid, quantitative and specific assay for screening test compounds, such as drugs, ligands (natural or synthetic), proteins, peptides and small organic molecules for their ability to inhibit the biological activity of macrophage migration inhibitory factor (MIF).

The present invention also relates to the drugs, ligands, proteins, peptides and small organic molecules identified by the screening assay of the present invention as capable of inhibiting biological activities of MIF.

In particular, the invention relates to methods of using such identified compounds in pharmaceutical compositions for the treatment of various conditions involving cytokine-mediated toxicity, which include, but are not limited to shock, inflammation, graft-versus-host disease, and/or autoimmune diseases.

Figure 1:
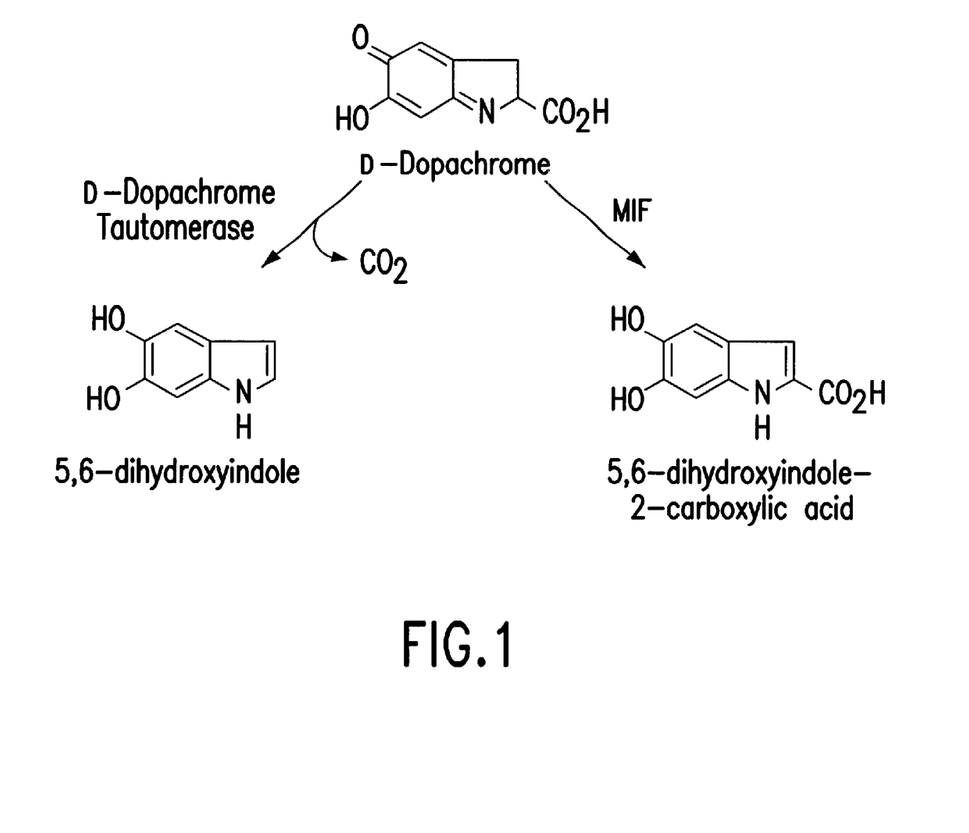
FIG. 1 is a scheme for the conversion of D-dopachrome catalyzed by D-dopachrome tautomerase and by MIF.

The invention is based, in part, on the surprising discovery and demonstration that MIF catalyzes a tautomerization reaction, and that assays for inhibitors of this tautomerase activity can be used to identify compounds that inhibit other biological activities of MIF. The enzymatic activity of MIF was uncovered during an investigation of the biochemical pathways of melanogenesis. The late stages of melanin biosynthesis involve the enzymatic conversion of L-2-carboxy-2,3-dihydroindole-5,6-quinone (L-dopachrome) into 5,6-dihydroxyindole-2-carboxylic acid (DHICA). A distinct enzyme activity isolated from bovine eye lens catalyzes the tautomerization of D-dopachrome, the non-physiological stereoisomer of the natural compound, L-dopachrome, to DHICA. (See FIG. 1). Purification and N-terminal sequence analysis of the protein responsible for this tautomerase activity for the non-naturally occurring substrate, D-dopachrome, identified the enzyme to be the bovine homolog of MIF. The enzymatic activity of purified, native MIF was confirmed by studies of recombinant human MIF, which was also found to catalyze selectively the same tautomerization reaction with D-dopachrome as substrate, but to be inactive toward L-dopachrome.

The present invention encompasses assays to identify compounds that inhibit the enzymatic activity of MIF which catalyzes the tautomerization of MIF-substrates, such as D-dopachrome to DHICA. In general, the assay is conducted in vitro by adding, mixing or combining MIF and a suitable substrate in the presence or absence of a test compound, and measuring the tautomerization of the substrate. The test compounds that inhibit tautomerization in the assay are identified as MIF inhibitors.

The present invention relates to the use of such identified inhibitors in pharmaceutical compositions designed to inhibit MIF biological activity for the treatment of cytokine toxicity-related disorders. The present invention encompasses the preparation of such pharmaceutical compositions and methods to use such compositions for the treatment of various conditions involving cytokine-mediated toxicity, which include, but are not limited to shock, inflammation, graft-versus-host disease, and/or autoimmune diseases.

3.1. Definitions

The following terms as used herein have the definitions indicated.

MIF refers to vertebrate forms of macrophage migration inhibitory factor and functional equivalents thereof, including but not limited to MIF protein and lysates containing MIF activity whether obtained from vertebrate tissue sources, including, but not limited to human, bovine, rat, mouse and chicken tissues, or from recombinant sources of MIF protein expressed by genetic engineering.

MIF tautomerase activity, MIF dopachrome tautomerase activity and MIF tautomerization activity all refer to the same enzymatic activity of MIF that is the ability of MIF to catalyze the tautomerization of a MIF-substrate.

MIF substrate refers to (a) D-dopachrome [D-3,5-dihydro-6-hydroxy-5-oxo-2H-indole-2-carboxylic acid], (b) D-dopachrome-methyl ester [D-3,5-dihydro-6-hydroxy-5-oxo-2H-indole-2-carboxylic acid methyl ester], or (c) L-dopachrome-methyl ester [L-3,5-dihydro-6-hydroxy-5-oxo-2H-indole-2-carboxylic acid methyl ester], or derivatives thereof.

Test compounds or test substances or test inhibitors refers to drugs, ligands (natural or synthetic), proteins, peptides or small organic molecules to be tested for their ability to inhibit the tautomerase activity of MIF.

5. DETAILED DESCRIPTION OF THE INVENTION

The present invention relates to rapid and quantitative methods for screening compounds that inhibit the biological activities of MIF. The assays of the present invention involve measuring the ability of a test substance to inhibit the MIF-catalyzed tautomerization of specific MIF-substrates. The test substances or test compounds include but are not limited to drugs, ligands (natural or synthetic), proteins, peptides or small organic molecules that inhibit the ability of MIF to enzymatically catalyze the tautomerization reaction. Those test substances which are identified as inhibitors of MIF enzymatic activity will be candidates for inhibitors of MIF biological activity, including but not limited to MIF inflammatory and immunological activities.

The present invention further relates to those drugs, ligands, proteins, peptide or small organic molecules identified as inhibitors of MIF enzymatic activity. In addition, the present invention relates to methods for the use of the identified MIF inhibitors in pharmaceutical compositions to treat disorders related to cytokine-mediated toxicity, which include, but are not limited to shock, inflammation, graft-versus-host disease, and/or autoimmune disease. The inhibitors may also have utility in that they act in an anti-inflammatory or otherwise beneficial capacity by increasing the therapeutic efficacy of glucocorticoids, whether such glucocorticoids are present endogenously or exogenously administered.

5.1. Screening Assay to Identify Inhibitors of MIF Activity

The present invention relates to a rapid, quantitative and specific assay for screening test compounds, such as drugs, ligands, proteins, peptides or small organic molecules which inhibit the ability of MIF to enzymatically catalyze the tautomerization of specific MIF-substrates. The screening assay of the present invention encompasses measuring the effect of a test substance on the ability of MIF to catalyze the tautomerization of a specific substrate.

The assay of the invention involves preparing a reaction mixture of MIF and the MIF-substrate in the presence and absence of the test substance or test compound. Tautomerization of the MIF-substrate is measured. Compounds that inhibit MIF-catalyzed tautomarization are the candidate compounds that can be used in accordance with the invention. While any order of addition of the reaction components can be utilized, it is preferred to add the MIF-substrate to a mixture of MIF and the test compound, or to add MIF to a mixture of the MIF-substrate and the test compound. Such order of additions would facilitate readout, since the assay reaction will not proceed until both the catalyst and substrate components are combined.

The assay may be formatted as a homogeneous assay, e.g., with all components in solution, or as a heterogenous assay; e.g., wherein either MIF or the MIF-substrate is immobilized on a solid support.

Reaction components and conditions that may be used in the screening assays of the invention include but are not limited to the tautomerization reactions described in Rosengren, E., R. Bucala, P. Aman, L. Jacobsson, G. Odh, C. N. Metz and H. Rorsman, February 1996, J. Molecular Medicine, Volume 2; 143 to 149 and Aroca et al., 1992 Eur. J. Biochemistry 208:155–163 each of which is incorporated by reference herein in its entirety.

Sources of MIF may include, but are not limited to, mammalian tissue, i.e., human, chicken, bovine, mouse, and rat tissue. Bovine tissue, i.e., eye lens is a source of preformed bioactive MIF protein. Hepatocytes are also an abundant source of preformed bioactive MIF protein. In a preferred embodiment of the present invention, the source of MIF protein is a recombinant form of MIF. A procedure for the purification of pure, bioactive recombinant MIF has recently been described and is incorporated herein by reference in its entirety (Bernhagen et al., 1994, Biochemistry 33:14144–14155). Methods to generate and purify bioactive recombinant murine or human MIF are described in Section 6 herein.

MIF-substrates that can be used in the assay include, but are not limited to, D-dopachrome, D-dopachrome methyl ester and L-dopachrome methyl ester. D-dopachrome is the non-naturally occurring D-isomer of L-2-carboxy-2,3-dihydroindole-5,6-quinone (L-dopachrome). The methyl esters of the D- and L-isomers are better tautomerase substrates for MIF than D-dopachrome in the sense that they are much more rapidly tautomerized. These substrates are generally formed immediately prior to conducting the assay, by oxidation of the corresponding phenylalanine analog; e.g., D-DOPA [or D-3-(3,4-dihydroxyphenylalanine] is oxidized to D-dopachrome [D-3,5-dihydro-6-dihydroxy-5-oxo-2H-indole-2-carboxylic acid]. In a preferred embodiment of the present invention, L-dopachrome methyl ester is used as the MIF-substrate in the screening assay. In another embodiment of the present invention, D-dopachrome methyl ester may be used as the MIF-substrate in the screening assay.

In one embodiment of the invention, an appropriate reaction mixture is prepared containing a bioactive form of MIF, in the presence or absence of a test compound, and an MIF-substrate, e.g., D-dopachrome. The ability of the test compound to inhibit the enzymatic activity of MIF is directly determined by measuring the conversion of the orange-colored D-dopachrome substrate to colorless DHICA. For example, the colored MIF substrate can be prepared immediately prior to assay by oxidizing a colorless DOPA derivative to form the colored substrate, D-dopachrome. The test compound and bioactive MIF is added to the colored MIF-substrate. Tautomerization of the MIF substrate by MIF results in a non-colored solution of DHICA and the conversion can be monitored, for example, spectrophotometrically over a defined period, for instance one minute. The presence of a test compound which inhibits the tautomerization activity of MIF results in a solution which maintains the D-dopachrome color. Therefore, the ability of a test compound to inhibit MIF activity can be alternatively visualized calorimetrically, or quantitated spectrophotometrically. For example, the tautomerization of D-dopachrome to DHICA is readily determined spectrophotometrically by measuring the rate of decrease of the iminochrome absorbance at a wavelength of 475 nm. However, the invention is not limited to spectrophotometric means for measuring tautomerization, and any appropriate method, e.g., HPLC resolution of products and substrates can be used.

In a preferred embodiment of the invention the assay of the invention involves adding a test compound to a reaction mixture containing about 0.5 mM of the MIF-substrate L-dopachrome methyl ester. This MIF-substrate is prepared immediately prior to assay by oxidation of L-DOPA methyl ester with periodate to yield the colored substrate L-dopachrome methyl ester. Approximately 50–250 ng of recombinant MIF is added to 1 ml of the substrate solution. The reaction is assayed directly in a cuvette by measuring the decrease of absorbance at 475 nm, or 550 nm for substrate concentrations higher than 0.5 mM. The resulting reaction product is the colorless compound 5,6-dihydroxyindole-2-carboxylic acid methyl ester (DHICA-ME). Test compounds which inhibit the decrease in absorbance are inhibitors of MIF D-dopachrome tautomerase activity and thereby identified as candidate inhibitors of inflammation-related or immune-related activities of MIF.

This assay offers several advantages. The assay provides a rapid, quantitative and specific means to measure the enzymatic activity of MIF. This assay provides a rapid screening procedure to identify inhibitors of the enzymatic activity of MIF. Those inhibitors identified will serve as candidate inhibitors of other biological activities of MIF, such as immunomodulatory activity.

5.2. Inhibitors of MIF Activity

The present invention also relates to those compounds, such as drugs, ligands (natural or synthetic), proteins, peptides, or small organic molecules, identified as inhibitors of the biological activity of MIF.

By way of explanation, but not limitation, in one embodiment of the invention, certain MIF inhibitors might inhibit the tautomerization of the substrate by competing with the substrate for MIF binding. Certain of these compounds are thought to interact with MIF but not to be tautomerized due to their specific structural features. These direct competitors include, but are not limited to, the D- and L-forms of a-methyl dopachrome methyl ester. The use of this type of inhibitor of MIF also has utility in targeting the tautomerase-related substrate binding site of MIF in order to bring a second functional element of a bi-functional inhibitor into effective molecular registration or steric alignment to inhibit the inflammatory or immunomodulatory activity of MIF.

In another embodiment of the invention, certain MIF inhibitors inhibit the tautomerization reaction by interacting with an epitope of MIF that is critical for enzymatic activity, for instance the amino terminus. An example of this embodiment of the invention is glutathione. Another example of this embodiment of the invention is the MIF inhibitor trypanothione, which is two molecules of glutathione covalently linked by a spermidine bridge. The use of this type of inhibitor of MIF also has utility in targeting the amino terminus of MIF in order to bring a second functional element of a bi-functional inhibitor compound into effective molecular registration or steric alignment to inhibit the inflammatory or immunomodulatory activity of MIF.

Examples of compounds within the scope of the invention are shown below:

I

X = H, F, Cl, Br, OH, OR'
Y = H, F, Cl, Br, OH, OR'

II

Q = H, F, Cl, Br, OH, OR'
X = H, F, Cl, Br, OH, OR'
Y = H, F, Cl, Br, OH, OR'
Z = NH, NR", $CH_2$, O, S, SO, $SO_2$

III

X = H, F, Cl, Br, OH, OR'
Y = H, F, Cl, Br, OH, OR'
Z = $CH_2$, NH, NR", O, S, SO, $SO_2$

IV

Y = H, F, Cl, Br, OH, OR'
X = H, F, Cl, Br, OH, OR'
Z = N, C—$CH_3$

V

Y = H, F, Cl, Br, OH, OR'
X = H, F, Cl, Br, OH, OR'
Z = N, C—$CH_3$

VI

X = H, F, Cl, Br, OH, OR'
Y = H, F, Cl, Br, OH, OR'

VII

X = H, F, Cl, Br, OH, OR'
Y = H, F, Cl, Br, OH, OR'
Z = NH, NR", $CH_2$, O, S, SO, $SO_2$

VIII

X = H, F, Cl, Br, OH, OR'
Y = H, F, Cl, Br, OH, OR'

IX

X = $CH_2$, O
Y = H, F, Cl, Br, OH, OR'
Z = N, C—$CH_3$

Wherein Q, X, Y and Z are defined above for each series of compounds, and R, R' and R" are each independently alkyl groups ($C_1$–$C_{20}$); preferably lower alkyl groups ($C_1$–$C_4$). Moreover, the invention encompasses pharmaceutically acceptable salts of these compounds.

5.2.1. Synthesis of Compounds

The compounds of the present invention can be synthesized in accordance with standard organic chemical techniques using readily/commercially available starting materials.

Compounds of series I are accessible by oxidation of the appropriate m-hydroxyphenylaline derivative with periodate or other suitable oxidant. For example, I (X=Y=OH) is available from the commercially available DL-threo-β-(3,4-dihydroxyphenyl)serine (Sigma). Other m-hydroxyphenylalines are available by transformations of 3-hydroxy-4-substituted cinnamic acids.

Compounds of series II (Z=NH or NR, X=OH) are accessible by reduction of compounds of series I with dithionite or other suitable reducing agent, followed in the case of Z=NR by alkylation of the nitrogen with R-halide. Compounds of series II (Z=CH$_2$) are accessible by transformations of appropriately 5,6-substituted indene or 1- or 2-indanone derivatives. Compounds of series II (Z=O or S) are accessible by transformations of appropriately 5,6-substituted benzofuran or thianaphthene derivatives, respectively. Compounds of series II (Z=—SO or —SO$_2$) are prepared by oxidation of II (Z=S) with hydrogen peroxide, peracids, or periodate under appropriate conditions.

Compounds of series III are accessible by treatment of corresponding compounds of series II (Q=Cl or Br) with a suitable base to effect β-elimination of the halogen.

Compounds of series IV (Z=N, Y=OH or OR') are accessible from kojic acid benzyl ether (2-hydroxymethyl-5-benzyloxy-4-pyranone) by reaction with β-alanine ethyl ester to give 2-hydroxymethyl-5-benzyloxy-4-pyridone-1-propionic acid ethyl ester; the hydroxymethyl group is oxidized to the aldehyde, 2-formyl-5-benzyloxy-4-pyridone-1-propionic acid ethyl ester, with chromium trioxide pyridine complex, and cyclization is affected by treatment with a base such as lithium diisopropylamide to give IV (Z=N, X=OH, Y=OCH$_2$Ph). From the latter, Compounds IV (X=OH) may be prepared by treatment with appropriate reagents for conversion of hydroxy to halogen, e.g., diethylaminosulfur trifluoride, thionyl chloride, or thionyl bromide. For compounds IV (Y=halogen), 2-formyl-5-(2-tetrahydropyranyl)oxy-4-pyridone-1-propionic acid ethyl ester, prepared from 2-hydroxymethyl-5-(2-tetrahydropyranyl)oxy-4-pyranone by reaction with β-alanine ethyl ester followed by oxidation with chromium trioxide pyridine complex, is hydrolyzed in mild acid to 2-formyl-5-hydroxy-4-pyridone-1-propionic acid ethyl ester, which is treated with an appropriate dehydroxyhalogenation agent such as diethylaminosulfur trifluoride, thionyl chloride, or thionyl bromide to give 2-formyl-5-halogeno-4-pyridone-1-propionic acid ethyl ester, which is then further converted as in the case of Y=benzyloxy.

Compounds of series IV (Z=C—CH$_3$, X=OH) are preparable from the corresponding 4-substituted-5-hydroxy-2-methylbenzaldehyde derivative by treatment with base to form the phenoxide anion, followed by cyclization with an acrylic ester. Compounds of series IV (Z=C—CH$_3$, X=F, Cl, or Br) are preparable by treatment of the appropriate compound of series V (see below) with the corresponding hydrogen halide in a non-hydroxylic solvent; subsequent treatment with a lower alkoxide affords compounds of series V (Z=C—CH$_3$, X or OR'), which alternatively are accessible by treatment of IV (Z=C—CH$_3$, X=OH) with an alkyl halide and a non-nucleophilic base.

Compounds of series V (Z=N) are accessible by treatment of corresponding compounds of series II (X=Cl or Br) with a suitable base to effect β-elimination of the halogen. Compounds of series V (Z=C—CH$_3$) are preparable from the corresponding 4-substituted-5-hydroxy-2-methylbenzaldehyde derivative by treatment with base to form the phenoxide anion, followed by cyclization with diethyl methylenemalonate to form a derivative of IV (Z—C—CH$_3$, R=Et, X=OH) bearing a second carbethoxy group geminal to the carboxylic group depicted in IV; this is then subjected to hydrolysis, decarboxylation and elimination preferably under acidic conditions to form compounds of series V (Z=C—CH$_3$, R=H) which may be re-esterified.

Compounds of series VI are accessible from the corresponding 6,7-substituted quinoline derivative by treatment with benzoyl chloride and sodium cyanide to give the 1-benzoyl-2-cyano-1,2-dihydro derivative, followed by hydrogenation to give the 1-benzoyl-2-cyano-1,2,3,4-tetrahydro derivative; this is hydrolyzed under basic or acidic conditions to give the corresponding 6,7-substituted-1,2,3,4-tetrahydroquinoline-2-carboxylic acid, which may then be converted to an ester, e.g., the methyl ester. Dehydrogenation at the 1,2-position is effected by treatment with an oxidant, a halogenation agent, or a sulfonylation agent, followed by base.

Compounds of series VII are accessible from compounds of series III by treatment with an appropriate carbenoid or methylene transfer reagent, e.g., by treatment with diazomethane, or by treatment with diiodomethane in the presence of zinc dust, or by treatment with bromoform in the presence of potassium tert-butoxide followed by debromination of the resulting bibromomethano derivative, e.g., using zinc in acetic acid.

Compounds of series VIII are preparable from compounds of series III (Z=CH$_2$) by treatment with an epoxidizing agent such as m-chloroperbenzoic acid.

Compounds of series IX (X=O) are likewise preparable from compounds of series V by treatment with an epoxidizing agent such as m-chloroperbenzoic acid. Compounds of series IX (X=CH$_2$) are preparable from compounds of series V under suitable methylene transfer conditions, e.g., by treatment with diazomethane.

5.3. Pharmaceutical Formulations and Routes of Administration

The compounds identified by the screening assay of the present invention which inhibit MIF tautomerase activity are good candidates for the inhibition of MIF immunomodulatory activity. The identified compounds of the present invention have utility in pharmacological compositions for the treatment of various conditions involving cytokine-mediated toxicity, which include, but are not limited to shock, inflammation, graft-versus-host disease, and/or autoimmune diseases. An identified compound can be administered to a human patient, by itself, or in pharmaceutical compositions where it is mixed with suitable carriers or excipients at doses to treat or ameliorate various conditions involving cytokine-mediated toxicity, which include, but are not limited to shock, inflammation, graft versus host disease, and/or autoimmune diseases. A therapeutically effective dose further refers to that amount of the compound sufficient to inhibit the biological activity of MIF. Techniques for formulation and administration of the compounds of the instant application may be found in "Remington's Pharmaceutical Sciences" Mack Publishing Co., Easton, Pa., latest addition.

5.3.1. Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than systemic manner, for example, via injection of the compound directly at the site of inflammation, often in a depot or sustained release formulation.

Furthermore, one may administer the drug in a targeted drug delivery system, for example in a liposome coated with an anti-MIF receptor antibody. The liposomes will be targeted to and taken up selectively by cells expressing MIF receptor.

5.3.2. Composition/Formulation

The pharmaceutical compositions of the present invention may be manufactured in a manner that is itself known, e.g., by means of conventional mixing, dissolving, drageemaking, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are usually known in the art.

For oral administration, the compounds can be formulated readily by combining the active compounds with pharmaceutically acceptable carriers well known to those in the art.

Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the MIF inhibiting compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in Remington's Pharmaceutical Sciences, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydrolodide, acetate, citrate, tartrate, malate sales, and the like.

5.3.3. Effective Dosage

Pharmaceutical compositions suitable for use in the present invention include compositions wherein the active ingredients are contained in an effective amount to achieve its intended purpose. More specifically, a therapeutically is effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the MIF activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical, pharmacological, and toxicological procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50–90% inhibition of the tautomerase activity using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

5.3.4. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

6. EXAMPLE

Expression and Purification of Bioactive Recombinant Murine and Human MIF 6.1. Materials and Methods 6.1.1. Materials Reagents for polymerase chain reaction (PCR), reverse transcription (RT), and other molecular biology techniques were purchased from Gibco BRL (Grand Island, N.Y.) unless stated otherwise. PCR buffer was from Perkin Elmer Cetus (Norwalk, Conn.); RNAse inhibitor "rRNasin" was obtained from Promega (Madison, Wis.); RNAzol™B was from TEL-TEST, INC. (Friendswood, Tex.); and oligonucleotides were purchased from OLIGOS ETC., INC. (Wilsonville, Oreg.). Manual DNA sequencing was performed with the SEQUENASE$^R$ 2.0 system (United States Biochemical, Cleveland, Ohio, Tabor & Richardson, 1987). For automated DNA sequencing, the Taq DyeDeoxy™ Terminator Cycle Sequencing Kit (Applied Biosystems Inc., Foster City, Calif.) was utilized. Western blotting was performed following a modification of the method by Anderson et al. (1982, Electrophoresis 3:135). Sodium dodecylsulfate-polyacrylamide gel electrophoresis (SDS-PAGE) and Western blotting reagents were from Pierce (Rockford, Ill.). Polyclonal anti-rmuMIF antiserum was prepared from rabbits immunized with purified rmuMIF. Thioglycollate broth (Difco, Detroit, Mich.) was prepared according to the manufacturer's recommendation, autoclaved, and stored protected from light at room temperature. E. coli O111:B4 LPS and polymyxin B were purchased from Sigma (St. Louis, Mo.). LPS was resuspended in pyrogen-free water, vortexed, sonicated, aliquoted (5 mg/ml), and stored at −20° C. Serial dilutions of LPS were prepared in pyrogen-free water and sonicated (Branson 3210, Danbury, Conn.) for 10 min prior to use.

6.1.2. Molecular Cloning of Murine and Human MIF

Murine MIF was cloned from the mouse anterior pituitary cell line AtT-20/D16v-F2 (American Type Culture Collection, Rockville, Md.). Cells were plated at $1 \times 10^6$ cells/ml in DMEN containing 50 µg/ml gentamicin (Gibco BRL), and 10% heat-inactivated fetal bovine serum (FBS) (HyClone, Logan, Utah). After 3 h of incubation at 37° C. in a humidified atmosphere with 5% $CO_2$, non-adherent cells were removed and the remaining adherent cells washed twice with DMEM/10% FBS. LPS (50 µg/ml) then was added and the cells were incubated for 16 h. At the end of this time, cell culture medium was removed and total RNA was isolated with RNAzol™B according to the manufacturer's instructions. One μg of RNA was reverse transcribed using oligo $(Dt)_{12-18}$ and M-MLV reverse transcriptase in a 50 μL reaction. Five μL of cDNA was amplified by PCR (32 cycles; 1 min at 94° C., 1 min at 55° C., 1 min at 72° C.) using MIF primers. A single DNA amplification product of expected size was obtained and purified using the GENE CLEAN II$^R$ Kit (BIO 101 Inc., La Jolla, Calif.). The cDNA then was cloned into the plasmid pT7Blue and transformed into Nova Blue competent *E. coli* using the pT7Blue T-Vector Kit (Novagen, Madison, Wis.). Recombinant DNA was prepared from multiple white colonies using the Plasmid Magic™ Minipreps DNA Purification System (Promega) and sequenced manually in a Sequi-Gen II Sequencing Cell (BIO-RAD, Hercules, Calif.).

For human MIF cloning, Jurkat H33HJ-JA1 cells (American Type Culture Collection) were plated at $1\times10^6$ cells/ml in RPMI containing 50 μg/ml gentamicin and 10% heat-inactivated FBS. After 3 h of incubation at 37° C. in a humidified atmosphere with 5% $CO_2$, non-adherent cells were removed and the remaining adherent cells washed twice with RPMI/10% FBS. Cells were incubated for another hour and the total RNA was isolated and subjected to RT as described above. NdeI/MIF- and BamHI/MIF-fusion primers (5'-CCATATGCCGATGTTCATCGTAAACAC-3' and 3'-CGGATCCTGCGGCTCTTAGGCGAAGG-5') were designed from a huMIF cDNA sequence (Weiser et al., 1989, Proc. Natl. Acad. Sci. USA 86: 7522) and used to amplify human MIF cDNA as described above. A single PCR product of predicted size was obtained, purified using the GENE CLEAN II$^R$ Kit, and ligated into the NdeI/BamHI-digested pET11b vector (Novagen). *E. coli* DH5α was transformed with the ligation mixture and the single recombinant colonies isolated after overnight growth. Plasmid DNA was prepared from eight clones and the MIF insert sequenced bi-directionally by automated methods using an ABI Model 373A DNA sequencer (Applied Biosystems Inc.).

6.1.3. Expression and Purification of Recombinant MIF

The recombinant pT7Blue clone containing muMIF cDNA was digested with the restriction enzymes NdeI and BamHI, and the MIF insert isolated and ligated into the NdeI/BamHI-digested pET11b vector (Novagen). *E. coil* DDH5α was transformed and the single recombinant colonies isolated and stored in 20% glycerol at -8° C. until use. Murine or human MIF-containing pET11b plasmid DNA then was prepared and used to transform the *E. coli* BL21 (DE3) expression strain (Novagen). One-liter cultures were grown at 37° C. until the optical density at 600 nm reached 0.6–0.8. Isopropyl 1-thio-β-D-galactopyranoside (IPTG) was added to a final concentration of 1 mM and the incubation continued at 37° C. for an additional 3 h. Bacteria then were harvested by centrifugation and the cell pellets frozen at -20° C. until use.

For protein purification, the bacterial pellets (corresponding to 50 ml of culture) were thawed and resuspended in 3.5 ml of Tris-buffered saline (50 mM Tris-HCl, 150 mM NaCl, pH 7.5). The bacteria were lysed by adding an equal volume of washed glass beads (106 microns; Sigma, G-8893) and vortexing the mixture vigorously for 10 min. Lysis was confirmed by examination under phase contrast microscopy. Glass beads were removed by centrifugation at 1000 g for 10 min and the bacterial extract then was centrifuged at 38000 g for 30 min. The supernatant, representing the cleared bacterial lysate, was sterile-filtered through a 0.45 μm and then a 0.22 μm membrane filter and subjected to MONO Q anion exchange chromatography using a Fast Protein Liquid Chromatography system (FPLC) (Pharmacia, Piscataway, N.J.). The Mono Q column was equilibrated with Tris-buffered saline. MIF was eluted with the same buffer in the first flow-through fractions (3 ml), which were pooled and placed on ice immediately. The MIF-containing fractions then were applied to a C8-SepPak reverse-phase (RP) column (Waters, Division of MILLIPORE, Milford, Mass.) that had been washed first with methanol, followed by water. Unbound material was eluted by washing the resin with 10 column volumes of water and 20% acetonitrile/water, respectively. MIF then was eluted with 6 column volumes of 60% acetonitrile/water, frozen at -80° C., lyophilized, and kept at -20° C. until use. For renaturation, MIF was dissolved at a concentration of 200–400 μg/ml in 20 mM sodium phosphate buffer (pH 7.2) containing 8 M urea and 5 mM DTT, and dialyzed against 20 mM sodium phosphate buffer (pH 7.2) containing 5 mM DTT, followed by 20 mM sodium phosphate buffer (pH 7.2) alone. Renatured MIF was sterile-filtered and kept at 4° C. until use. The LPS content of MIF preparations was determined by the chromogenic Limulus amoebocyte assay (Bio-Whittaker Inc., Walkersville, Md.). Attempts to purify rmuMIF from the cleared bacterial lysate by affinity chromatography with S-hexyl-glutathione-agarose beads (Sigma, H-7011) were performed following the method for single-step purification of protein/glutathione-S-transferase fusion constructs (Smith & Johnson, 1988, Gene 67: 31).

6.1.4. Purification of Native MIF

Two grams of mouse liver acetone powder (Sigma, L-8254) were resuspended in 20 ml of Tris-buffered saline, vortexed, and the insoluble material removed by centrifugation at 1000 g for 10 min. The supernatant, containing MIF and other hepatic proteins, was filtered (0.45 μm followed by 0.22 μm filter) and subjected to MONO Q/FPLC anion exchange chromatography as described above. MIF eluted with the first flow-through fractions (3 ml), which were pooled and applied to a Pro S cation exchange column (BIO-RAD) that was equilibrated with Tris-buffered saline. MIF eluted with Tris-buffered saline and the MIF-containing fractions again were recovered from the flow-through. The MIF fractions then were pooled and applied to a C8-SepPak cartridge. MIF was eluted with 60% acetonitrile/water, lyophilized, and stored as described above. Attempts to purify liver MIF from mouse liver supernatant by affinity chromatography with S-hexyl-glutathione-agarose beads were performed as described above.

6.1.5. Purification Characterization of MIF

SDS-polyacrylamide gel electrophoresis (SDS-PAGE) was performed in 18% gels under reducing conditions (Laemmli, 1970, Nature 227: 680). The gels were either stained with silver or processed further for Western blotting. For silver staining, gels first were fixed for 16 h in 50% methanol/10% acetic acid and then analyzed as described (Poehling & Neuhoff, 1981, Electrophoresis 2: 141). For Western blotting, proteins were transferred to nitrocellulose membrane (Schleicher & Schuell, Keene, N.H.) by electroblotting at 50 V and 150 mA for 16 h using CAPS-transfer buffer (10 mM CAPS, 20% methanol, pH 11.0). Membranes then were incubated with blocking buffer (50 mM Tris-HCl, 500 mM NaCl, pH 7.5, 5% non-fat dry milk, 0.05% Tween-20) followed by incubation with a 1:1000 dilution of polyclonal rabbit anti-rmuMIF antiserum in binding buffer (50 mM Tris-HCl, 500 mM NaCl, pH 7.5, 1% BSA, 0.05% Tween-20). After extensive washing in binding buffer, membranes were incubated with a 1:1000 dilution of horseradish peroxidase-conjugated goat anti-rabbit antibody (Pierce) in binding buffer, washed twice with binding buffer, twice with 50 mM Tris-Base (pH 7.5) containing 150 mM NaCl, and developed with chloronaphthol/$H_2O_2$ substrate. Pre-stained protein molecular weight ($M_r$) markers ranged from 2.5–43 kDa (Gibco BRL).

N-terminal MIF sequence was determined by Edman degradation (Allen, 1981 In: Sequencing of Proteins and Peptides, Elsevier, Amsterdam, New York) and automated gas-phase sequencing following a manufacturer's protocol (Applied Biosystems).

For N-glycosylation analysis, 0.1 µg of purified liver-derived MIF was incubated with the endoglycosidase PNGase F according to the manufacturer's instructions (New England BioLabs, Beverly, Mass.). Samples then were mixed 1:1 with Laemmli electrophoresis buffer, boiled for 5 min, and ¼ of the incubation mixture analyzed by SDS-PAGE/Western blotting as described above. To control for digestion efficiency, IgG light and heavy chains were digested in parallel and resolved on the same gel. Digestion was assessed to be complete after 3 h incubation with 5000 units/ml of PNGase F.

For analytical size exclusion chromatography, 40 µg of purified rmuMIF or rhuMIF was dissolved in 200 µl 20 mM sodium phosphate buffer (pH 7.2) containing 7 M GdnHCl. The sample was separated over a Superose 12 HR 10/30 column (Pharmacia), equilibrated with the same buffer, and eluted at a flow rate of 0.5 ml/min. Size markers were from BIO-RAD (1.35–670 Kda) and were chromatographed under the same conditions.

Mass spectrometric analysis (MS) of MIF was performed by matrix-assisted laser desorption ionization MS as described elsewhere (Hillenkamp & Karas, 1990, Meth. Enzymol. 193: 280) using a Shimadzu Kratos Kompact MALDI 3 V3.0.2 machine (Hannover, Germany). Twenty individual spectra were accumulated for each mass analysis. In addition, rmuMIF was analyzed by ion-spray mass spectroscopy (IS-MS) using an API III triple quadrupole mass spectrometer with an IonSpray™ interface (Sciex, Toronto).

Purified, renatured rmuMIF (20 µg/ml) and MIF-containing bacterial lysates (estimated MIF content: 50 µg/ml) were analyzed photometrically for glutathione-S-transferase (GST) activity by the method of Fjellstedt et al. (1973, J. Biol. Chem. 248: 3702) using 1,2-epoxy-3-(p-nitrophenoxy)propane (EPNP) as a substrate and bovine GST (Sigma, G-8386) as a positive control (Blocki et al., 1992, Nature 360: 269). In this assay system, bovine GST (400 µg/ml) was found to have an enzyme activity of 0.014 units/ml with respect to the substrate EPNP.

6.1.6. Bioactivity Profile

The macrophage/monocyte migration inhibitory activity of recombinant MIF was analyzed by studying the migration of human peripheral blood monocytes in modified Boyden chambers (Boyden, 1962, J. Exp. Med. 115: 453). Monocytes were isolated from heparinized venous blood of healthy donors and resuspended at a concentration of 2.5× $10^6$ cells/ml in Gey's balanced salts solution (Gibco BRL) containing 2% fatty acid-free bovine serum albumin (Sigma) and 20 mM Hepes (pH 7.2). MIT-containing (0.0001–10 µg/ml) solutions or buffer controls were placed in the lower compartment of the Boyden chamber, covered tightly by a polyvinylpyrrolidone-free polycarbonate filter (5-µm pore size, no. 155845, Costar Corp., Cambridge, Mass.) and monocytes (1×105) added to the compartment above the filter. The chambers then were incubated for 3 h at 37° C. in a humidified atmosphere with 5% $CO_2$. At the end of this time, the filters were recovered and the cells fixed and stained with Giemsa reagent. Monocytes then were counted as described previously (Sherry et al., 1992, Proc. Natl. Acad. Sci. USA 89: 3511).

TNAα production was quantitated in MIF-conditioned RAW 264.7 macrophage supernatants by L929 cell cytotoxicity as described previously (Wolpe et al., 1988, J. Exp. Med. 167: 570). RAW 264.7 macrophages were resuspended in RPMI/10% FBS, plated at 1×$10^6$ cells/ml, incubated for 3 hours at 37° C. in a humidified atmosphere with 5% $CO_2$, and washed twice with RPMI/1% FBS. Cells were incubated for 12–14 hours with various doses of MIF diluted in RPMI/1% FBS. At the end of each experiment, cell culture media were collected, centrifuged (10 min at 800 g), and supplemented with 1 mM PMSF. MIF-induced TNAα activity was measured immediately afterwards. Polyclonal rabbit anti-recombinant murine TNFα antiserum (50 µl/ml) blocked TNFα activity completely, and MIF did not contribute to TNFα activity as recombinant murine TNFα (rTNFα) (5 pg/ml to 1 µg/ml) cytotoxicity remained unchanged when rmuMIF (10 pg/ml to 10 µg/ml) or anti-rmuMIF antibody were added to L929 cells together with rTNFα.

Nitric oxide (NO) production was quantitated in MIF-conditioned RAW 264.7 and thioglycollate-elicited peritoneal exudate macrophage supernatants by measuring nitrite and nitrate content with the Griess reagent. RAW 264.7 macrophages were prepared and conditioned as described above. In some experiments, cells were incubated for 1 h with recombinant murine interferon-γ (IFN-γ) (100 IU/ml) (Boehringer-Mannheim, Indianapolis, Ind.) prior to the addition of MIF. Thioglycollate-elicited peritoneal exudate macrophages were obtained from BALB/c mice that were injected intra-peritoneally 3–4 days previously with 2 ml of sterile thioglycollate broth. Cells were harvested under strict aseptic conditions by lavage of the peritoneal cavity with 5 ml of an ice-chilled 11.6% sucrose solution. After centrifugation (10 min at 800 g), cells were resuspended in RPMI/10% FBS and plated at a density of 2×$10^6$ cells/ml. After 3 h of incubation, non-adherent cells (i.e. PMNs, lymphocytes) were removed with RPMI/1% FBS and the remaining adherent cells conditioned with MIF as described for RAW 264.7 cells. Trace concentrations of contaminating LPS were neutralized by incubating MIF (1 and 10 µg/ml in cell culture media) with polymyxin B at a concentration of 10 and 100 ng/ml, respectively, for 30 min at room temperature under sterile conditions. The mixture was cleared by centrifugation and added to the prepared macrophage cultures. The polymyxin B concentration added was approximately a 1000-fold higher than necessary to neutralize the contaminating LPS present. For antibody neutralization of MIF activity, rmuMIF (1 and 10 µg/ml in cell culture media) was treated with 20 µL/ml of anti-rmuMIF or normal rabbit control serum and added to the macrophages as described above.

6.1.7. Conformational and Structural Stability Analysis

CD spectra were recorded on an Aviv Associates Model WP spectropolarimeter. The spectra represent the average of three scans recorded at 25° C. in the range between 190 nm and 250 nm and were collected at 0.25 nm intervals, with a band width of 1.5 nm and a time constant of 1.0 sec. The quartz cells (1 and 10 mm) used in all CD measurements were washed with 30% HCl in ethanol, rinsed with water and methanol, and dried before used. Protein concentrations were determined from stock solutions prepared in 20 mM phosphate buffer (pH 7.2) using the Bio-Rad protein assay (BIO-RAD). This assay was found to agree with values obtained by quantitative amino acid analysis. Thirty min before CD analysis, proteins were diluted from the stock solutions to a final concentration of 10 μM in 20 mM phosphate buffer (pH 7.2), unless stated otherwise. CD spectra are presented as a plot of the mean molar ellipticity per residue ([θ], deg cm$^2$ dmol$^{-1}$) versus the wavelength.

For unfolding experiments, MIF stock solutions dissolved in 20 mM phosphate buffer (pH 7.2) were mixed with increasing volumes of 8 M GdnHCl (molecular biology reagent grade, Sigma) prepared in 20 mM phosphate buffer (pH 7.2) so as to achieve a final protein concentration of 10 μM and the indicated final GdnHCl concentrations. Samples then were equilibrated at room temperature for 30 min prior to the recording of CD spectra.

6.2. Results 6.2.1. Cloning of Murine and Human MIF

N-terminal protein sequencing and cDNA cloning were used to identify the murine homolog of MIF among the proteins secreted by LPS-stimulated anterior pituitary cells. MuMIF cDNA was prepared from the total RNA of LPS-stimulated anterior pituitary cells (AtT-20) and amplified with MIF primers. MIF cDNA then was cloned into the pT7Blue T-vector and subjected to DNA sequence analysis. The muMIF cDNA sequence obtained from 6 plasmid clones was compared to a previously published human T-cell MIF cDNA (Weiser et al., 1989, Proc. Natl. Acad. Sci. USA 86: 7522). Murine MIF cDNA was found to display a 88.2% sequence homology to this huMIF sequence over a 348 nucleotide open reading frame and to be identical in sequence with recently reported murine 3T3 fibroblast, and murine embryonic eye lens MIF cDNAs (Lanahan et al., 1992, Mol. Cell. Biol. 12: 3919; Wistow et al., 1993, Proc. Natl. Acad. Sci. USA 90: 1272).

HUMIF cDNA was prepared by RT/PCR of RNA isolated from resting Jurkat H33HJ-JA1 T-cells. MIF cDNA was amplified with flanking primers bearing NdeI/BamHI restriction sites, thus enabling the subsequent cloning of the huMIF amplification product directly into a NdeI/BamHI-digested pET11b prokaryotic expression plasmid. Human MIF cDNA sequence then was obtained by sequencing both DNA strands of 8 independently derived E. coli clones. This Jurkat T-cell MIF sequence was found to be identical to a recently reported human fetal lens MIF cDNA (Wistow et al., 1993, Proc. Natl. Acad. Sci. USA 90: 1272) and to a glycosylation inhibition factor (GIF) cDNA (Mikayama et al., 1993, Proc. Natl. Acad. Sci. USA 90: 10056), but differed from the first reported human T-cell MIF sequence obtained from the T-CEMB cell line (Weiser et al., 1989, Proc. Natl. Acad. Sci. USA 86: 7522) by a single base change at position 318. This G→A substitution produces a conservative Ser$^{106}$→Asn$^{106}$ change in the deduced amino acid sequence and renders the human protein even more homologous with murine MIF. Murine pituitary MIF cDNA and human Jurkat cell cDNA exhibited 88.5% identity over a 348 nucleotide open reading frame and the amino acid sequences deduced for murine (AtT-20) and human (Jurkat) MIF were found to be 90% identical over the 115 amino acids. No apparent N-terminal signal sequences were evident in either the murine or the human proteins. MIF thus joins a growing list of cytokines, such as interleukin-1 (IL-1) (Rubartelli et al., 1990, EMBO J. 9:1503), basic fibroblast growth factor (bFGF) (Jackson et al., 1992, Proc. Natl. Acad. Sci. USA 89: 10691), and a secreted form of cyclophilin (Sherry et al., 1992, Proc. Natl. Acad. Sci. USA 89: 3511), which are released from cells by non-classical protein secretion pathways. Two potential N-glycosylation sites were found at positions 75 and 110 of the muMIF amino acid sequence and were at nearly identical positions in the human Jurkat MIF sequence (positions 73 and 110). Three cysteine residues (positions 57, 60, and 81) also were at identical places in the murine and human MIF predicted amino acid sequences.

6.2.2. Expression and Purification of Recombinant MIF from E. Coli

Recombinant muMIF and huMIF were expressed in E. coli by cloning murine and human MIF cDNA into the IPTG-inducible pET expression plasmid system. Initial attempts to express murine MIF from the pET15b vector, which created an N-terminal oligo-histidine fusion protein and allowed for facile purification of recombinant protein by ion metal affinity chromatography (IMAC), were unsuccessful because the protein was resistant to the subsequent thrombin cleavage necessary to remove the oligo-histidine leader. Thus, recombinant muMIF was expressed and then purified by conventional means and the muMIF cDNA subcloned into the plasmid pET11b. This produced a construct which bore a three amino acid (Met-Asp-Ser) leader sequence attached to the N-terminus of MIF. HUMIF also was expressed from the pET11b vector but was engineered by DNA amplification to begin at the second amino acid of the open reading frame, with the start methionine of MIF provided by the NdeI restriction site. The correct expression of MIF was verified by N-terminal amino acid sequencing of gel-purified protein (10 amino acids for muMIF), SDS-PAGE, and Western blotting with anti-AtT-20 MIF antibody. The pET11b-derived MIF was used for the subsequent purification of bioactive muMIF and huMIF.

Recombinant murine or human MIF were found to constitute 40% of the total supernatant protein of E. coli lysates. Anion exchange chromatography at pH 7.5 resulted in approximately an got purification of murina and human MIF. Subsequent application to a C8 reverse-phase column yielded pure protein for both the murine and the human recombinant proteins, as verified by the appearance of single bands of predicted $M_r$ (12.5 kDa) by SDS-PAGE/silver staining and by mass spectrometric analysis, infra. This simple and rapid two-step procedure was used to purify 1 mg of murine or human MIF per 50 ml of E. coli culture. After renaturation, 0.8–0.9 mg of soluble, bioactive recombinant MIF was obtained per 50 ml culture. The overall yield of MIF protein from total bacterial supernatant protein was estimated to be 20%. This two-step purification method was elected for reasons of simplicity and rapidity and to minimize protein losses by non-specific precipitation. Purification by C8 chromatography using a disposable, low volume push column also served to remove the LPS carried over from E. coli host cells. Recombinant MIF purified by these procedures contained no more than trace amounts of LPS (4–8 ng LPS per mg MIF).

6.2.3. Purification of Native MIF

To assess more precisely the biological activities of recombinant MIF, native MIF was also purified from mouse tissue. Pituitary cells yielded insufficient quantities of MIF protein for biochemical characterization, but Western blotting showed that the liver was an abundant source of MIF in vivo. MIF was purified from liver by a method similar to that used for recombinant MIF purification. Mono Q anion exchange chromatography resulted in partial purification and increased the relative MIF content by approximately 25-fold. Subsequent application to the C8 push column afforded almost pure MIF. Upon SDS-PAGE/silver staining analysis however, 5 additional bands were detected that could not be removed by varying the elution conditions of the RP chromatography. A Pro S cation exchange chromatography step therefore was added prior to the C8 step to remove these contaminants. The purity and homogeneity of liver MIF was established by SDS-PAGE/silver staining, Western blotting using anti-rmuMIF antibody, and mass spectrometric analysis. Laser desorption MS demonstrated a single protein species of $M_r$ 12,555. The MIF content of mouse liver acetone powder was estimated to be less than 0.1% of total protein and 2 grams of mouse liver powder were used to purify to homogeneity 50 µg native liver MIF.

6.2.4. Biochemical Characterization of MIF

The $M_r$ for liver murine MIF, rmuMIF, and rhuMIF were each between 12000 and 13000 as estimated by reducing SDS-PAGE. Two potential N-linked glycosylation sites were detected in the predicted amino acid sequence of murine and human MIF and thus the possibility that native muMIF was post-translationally glycosylated in vivo was investigated. Endoglycosidase F (PNGase F) digestion of purified liver MIF followed by reducing SDS-PAGE/Western blotting analysis showed no shift in the observed $M_r$, indicating the absence of significant N-glycosylation of native liver MIF.

Gel exclusion chromatography of GdnHCl-denatured recombinant MIF showed a $M_r$ of 14,256 and 13,803 for the murine and human proteins, respectively, indicating that MIF eluted predominantly as a monomer.

Laser desorption MS of MIF was performed to further assess glycosylation as well as the presence of any other significant post-translational modifications of MIF. Native MIF obtained from mouse liver was determined to have a $M_r$ of 12,555 (predicted MH$^+$ average mass of oxidized muMIF=12,503). By comparison, rmuMIF (which bore a 3 amino acid N-terminal leader sequence) was found to have a $M_r$ of 12,814 (predicted MH$^+$ average mass of oxidized rmuMIF=12,801). Ion-spray MS of rmuMIF yielded a similar mass ($M_r$=12,804). Using laser desorption MS, rhuMIF was found to have a $M_r$ of 12,521 (predicted MH$^+$ average mass of oxidized rhuMIF=12,475). Differences observed between the experimental and theoretical, predicted masses were within the margin of experimental error (0.1–1%) for these analyses. These data essentially ruled out the presence of significant post-translational modifications of either native or recombinant MIF protein.

A 12 kDa protein purified from rat liver bearing N-terminal homology with huMIF has been reported to bind to glutathione affinity matrix and to exhibit glutathione-S-transferase (GST) activity (Blocki et al., 1992, Nature 360: 269). Neither liver MIF nor rmuMIF was shown to specifically absorb to glutathione-modified matrix.

6.2.5. Bioactivity Profile

Purified rmuMIF displayed significant migration inhibitory activity when tested on human peripheral blood monocytes. A bell-shaped dose response curve was observed with peak activity occurring at 0.1 µg/ml. The precise basis for diminished inhibitory activity at high MIF concentrations is not known, but similar dose-response profiles have been observed for chemotactic cytokines (Sherry et al., 1992, Proc. Natl. Acad. Sci. USA 89: 3511).

Recombinant MIF was used to induce TNAα release by the murine RAW 264.7 macrophage cell line. Both rmuMIF and rhuMIF added at concentrations of 0.1–10 µg/ml caused the release of bioactive TNAα in the ng/ml range (Table I). Despite species-specific differences, rhuMIF at 1/µg/ml was found to be slightly more active than rmuMIF on murine macrophages. At the same concentration (1 µg/ml), the TNFα-inducing activity of MIF obtained from mouse liver was found to be higher than the activity of rmuMIF. When tested at a concentration of 0.1 µg/ml however, the TNFα-inducing activity of mouse liver MIF was identical to rmuMIF. Similar findings were obtained when thioglycollate-elicited mouse peritoneal macrophages were used to study MIF-induced TNFα release. Overall, the activity of purified native MIF was within the range observed for the recombinant proteins.

TABLE I

MIF-INDUCED SECRETION OF TNFα BY MOUSE MACROPHAGES[a]

Secretion of TNFα (ng/ml) induced by:

| MIF (µg/ml) | rmuMIF | rhuMIF | Native MIF |
| --- | --- | --- | --- |
| 10 | ND | 3.9 ± 2.8 | ND |
| 1 | 1.2 ± 0.1 | 3.4 ± 2.8 | 6.9 ± 3.4 |
| 0.1 | 0.2 ± 0.3 | 2.9 ± 2.4 | 0.2 ± 0.1 |
| 0.01 | 0 | ND | 0 |

[a]RAW 264.7 macrophages were prepared and incubated with MIF for 12–14 h as described in Section 6.1.6. supra. After the incubations, macrophage culture supernatants were removed, and analyzed by L929 cell toxicity assay for TNFα activity. TNFα measurements were performed in duplicate and TNFα activity is expressed as the difference between the level produced by MIF-stimulated cells and by non-stimulated control cells. Data are the mean ± SEM of at least three separate experiments.
ND: not determined.

Native and recombinant MIF also induced NO production in macrophages. However, significant MIF-induced NO production was observed only when macrophages were incubated with IFN-γ prior to stimulation with MIF. In RAW 264.7 macrophages, the activity of rhuMIF at 1 µg/ml was found to be approximately 4-fold higher than rmuMIF. Native MIF obtained from mouse liver also was more active in this assay than rmuMIF. MuMIF stimulated NO production from IFN-γ-primed, thioglycollate-elicited peritoneal exudate macrophages at levels which were comparable with those observed in RAW 264.7 cells. However, liver MIF at 1 µg/ml was not found to be more active than rmuMIF on this macrophage cell type.

The synthesis of NO by macrophages is induced by ≧10 ng/ml of LPS and this effect is potentiated by IFN-γ priming (Ding et al., 1988, J. Immunol. 141: 2407). To exclude the possibility that the trace amounts of LPS present in recombinant MIF preparations contribute to NO production, MIF-induced NO release was tested after neutralization of LPS with a large excess of polymyxin B. The production of NO was not reduced by polymyxin B treatment, arguing against a potentiating role for LPS in the stimulation of macrophages by MIF. In further control studies, the addition of neutralizing anti-rmuMIF antiserum (20 µl/ml) inhibited rmuMIF (1 and 10 µg/ml)-induced NO production, further confirming the specificity of macrophage stimulation by recombinant MIF.

7. Example

Inhibition of MIF Tautomerase Activity 7.1. Inhibition with Glutathione

In order to determine the inhibitory effects of glutathione on the enzymatic activity of MIF, the following in vitro assay was carried out. A reaction mixture containing 0.5 mM of the MIF-substrate L-dopachrome methyl ester was prepared immediately prior to the assay by oxidation of L-DOPA methyl ester with periodate. A 1 mM solution of L-DOPA methyl ester was prepared in Reaction Buffer (10 mM sodium phosphate, pH 6, containing 0.5 mM EDTA). L-DOPA methyl ester was oxidized to colored L-dopachrome methyl ester by adding 10% (V/v). of a 20 mM aqueous solution of potassium periodate, following a 1:2 dilution with Reaction Buffer. After approximately 10 minutes, the color remained stable and the substrate solution was ready for use in the assay.

The test compound, reduced glutathione, was added in concentrations of 0.1 mM, 0.5 mM, 1.0 mM, and 2.0 mM to separate cuvettes containing the substrate solution. Approximately 100 ng of purified recombinant human MIF was added to each cuvette. The absorbance at 475 nm of each sample cuvette was measured over the first 30 seconds to 1 minute and the initial rate of change in absorbance, indicating reaction rate or velocity, was recorded. This decrease in absorbance following addition of recombinant human MIF was used to determine the tautomerase activity of recombinant human MIF in the presence of glutathione. Results are shown in Table II below.

TABLE II

| Glutathione in Assay (mM) | % Inhibition |
|---|---|
| 0 | 0% |
| 0.1 | 14% |
| 0.5 | 69% |
| 1.0 | 95% |
| 2.0 | 100% |

At 0.5 mM to 2.0 mM concentrations, glutathione was an effective inhibitor of MIF tautomerase activity. These results indicate that binding of glutathione to MIF either competes for the active site with the substrate, or disturbs MIF structure by binding to another site in a way that renders the MIF-substrate:MIF interaction enzymatically unproductive.

7.2. Inhibition of Mutagenization of the Amino Terminus of MIF

In order to investigate the influence of the native MIF amino terminus on MIF tautomerase activity, an amino-terminal mutation of murine MIF was expressed in *E. coli* and assayed for tautomerase activity.

The coding region of murine MIF was mutagenized by the addition of a three amino acid extension sequence: methionine-aspartate-serine, to the native amino terminus. The altered coding region of murine MIF was expressed in *E. coli* and the expressed protein was purified and assayed for MIF tautomerase activity as described above. Expression of this altered gene resulted in an MIF protein entirely lacking. tautomerase activity. The expression of human MIF bearing an unaltered, native amino-terminus in the same *E. coli* system resulted in a highly active MIF, the tautomerase activity of which could be detected even in crude bacterial lysates, without purification.

The complete loss of MIF tautomerase activity by amino-terminal extension suggests a crucial influence of this region on MIF tautomerase activity. One possible explanation is that the structure of MIF may be so disturbed by altering the amino-terminus that substrate binding is impossible. Alternatively, the amino terminal extension may disturb the conformation of the active site such that tautomerization of bound substrates is no longer effectively catalyzed.

8. Example

Inhibition of MIF Tautomerization Activity by Compounds 2b, 3b, 4b and 5b

The ability of compounds 2b [L-3,5-dihydro-6-hydroxy-2-methyl-5-oxo-2H-indole-2-carboxylic acid], 3b [D/L-3,5-dihydro-6-hydroxy-2-methyl-5-oxo-2H-indole-2-carboxylic acid], 4b [L-3,5-dihydro-6-hydroxy-2-methyl-5-oxo-2H-indole-2-carboxylic acid methyl ester], and 5b [D/L-3,5-dihydro-6-hydroxy-2-methyl-5-oxo-2H-indole-2-carboxylic acid methyl ester] (shown below) to inhibit MIF tautomerization activity was assayed in vitro.

| | D/L | $R_1$ | $R_2$ |
|---|---|---|---|
| 1a, 1b: | L | H | $CH_3$ |
| 2a, 2b: | L | $CH_3$ | H |
| 3a, 3b: | DL | $CH_3$ | H |
| 4a, 4b: | L | $CH_3$ | $CH_3$ |
| 5a, 5b: | DL | $CH_3$ | $CH_3$ |

8.1. Materials and Methods

The general method of performing an assay for MIF dopachrome tautomerase activity, described in more detail below, begins with the oxidation of a percursor of the MIF-substrate (e.g., DOPA-related Compound 1a [L-3-(3, 4-dihydroxyphenyl) alanine methyl ester] above) and, if required, the similar oxidation of precursors of the test inhibitors (e.g., the DOPA-related Compounds 2a [L-3-(3, 4-dihydroxyphenyl)-2-methyl alanine], 3a [D/L-3-(3,4-dihydroxyphenyl)-2-methyl alanine], 4a [L-3-(3,4-dihydroxyphenyl)-2-methyl alanine methyl ester] and 5a [D/L-3-(3,4-dihydroxyphenyl)-2 methyl alanine methyl ester] above). This oxidation of each precursor compound with sodium periodate generates the corresponding orange-colored dopachrome derivative; specifically, a preferred MIF-substrate (Compound 1B above) and the test inhibitors (Compounds 2b, 3b, 4b, and 5b above). Upon addition of MIF, the MIF-substrate (Compound 1b [L-3,5-dihydro-6-hydroxy-5-oxo-2H-indole-2-carboxylic acid methyl ester]) undergoes tautomerization resulting in a colorless product. In the presence of the test inhibitors (Compounds 2b, 3b, 4b, and 5b), decolorization of MIF-substrate (Compound 1b) was retarded. Test compounds 2b, 3b, 4b, and 5b themselves were unreactive in this tautomerization reaction; that is, they were not tautomerized and correspondingly decolorized by MIF dopachrome tautomerase activity if they were substituted for the MIF-substrate in this assay method.

In a preferred MIF dopachrome tautomerase activity assay procedure, the DOPA-related precursors (Compounds 1a, 2a, 3a, 4a, and 5a above) are prepared as 10 mM stock solutions in Assay Buffer (10 mM sodium phosphate, pH 6.0). About 10 minutes before the tautomerization assay, 1.0 ml of each stock solution was diluted with 8 ml of Assay Buffer, and 1.0 ml of sodium periodate stock solution (20 mM in water) was added to initiate the oxidation of the diluted precursors, thus generating each respective dopachrome derivative (i.e., Compounds 1b, 2b, 3b, 4b, and 5b) at a final concentration of 1 mM. To perform the actual tautomerization assay, 0.5 ml of the 1 mM solution of the MIF-substrate (i.e., Compound 1b) was mixed with 0.5 ml of Assay Buffer (no inhibitor control reaction) or 0.5 ml of the 1 mM dilution of the test inhibitor (e.g., Compounds 2b, 3b, 4b, or 5b), followed by addition of 10 μl of recombinant MID solution from a 20 µg/ml stock. As described in Section 7 (above), the decrease in absorbance at 475 nm in 1 minute was measured as an index of tautomerase activity, and the percent inhibition of this decrease in the presence of Compounds 2b, 3b, 4b and 5b was calculated from the spectrophotometric data by standard methods.

8.2. Results

The results of this assay are shown in the table below:

TABLE III

| Inhibitor | % Inhibition of MIF Tautomerase Activity |
|---|---|
| 2b | 35 |
| 3b | 29 |
| 4b | 34 |
| 5b | 45 |

When present at the same concentration as the MIF-substrate, test inhibitors 2b, 3b, 4b, and 5b each inhibited MIF tautomerization activity as measured by the inhibition of the decrease in dopachrome-specific absorbance. These results indicate that abstraction of the α-hydrogen of the dopachrome-related MIF-substrate is a critical step in the MIF-catalyzed tautomerization, and that test compounds lacking this hydrogen atom (e.g., those with an α-methyl substitution) are effective inhibitors of MIF dopachrome tautomerase activity. This inhibition of MIF dopachrome tautomerase activity by these test compounds probably involves competition against the MIF-substrate for the active site in the MIF protein.

9. Example

Inhibition of MIF Tautomerization Activity by Glycation of Lysine Residues

Upon prolonged exposure to glucose or another reducing sugar, in vivo or in vitro, proteins and other amino-containing biomolecules becomes spontaneously modified by covalently attached sugar-derived adducts (Bucala and Cerami, 1992, Adv. Pharmacol. 23;1–34). The chemistry of this rocess is broadly known as the Maillard reaction, wherein susceptible protein amino groups, such as the peptide amino-terminus and the ε-amino moieties of lysine residues for example, first condense with the reactive carbonyl moiety of a reducing sugar to form a readily reversible Schiff base. This initial adduct can spontaneously rearrange to generate the Amadori product (or Heyns product, depending on the specific sugar involved), which is stable.

Purified recombinantly-produced human MIF protein was glycated by incubation in aqueous buffer in the presence of 0.5 M glucose, typically for 6 weeks in the dark at 37° C. under a nitrogen atmosphere to ensure complete glycation of susceptible residues (although other spontaneous glycation conditions will serve to glycate the protein without departing from the essence of the invention) and tested for D-dopachrome tautomerase activity by the method of Section 7 or Section 8. This glycated or AGE-modified (AGE-MIF) showed no D-dopachrome tautomerase activity. The AGE-MIF was recovered and analyzed by matrix-assisted laser desorption ionization mass spectroscopy and determined to have a mass consistent with three-fold Amadori product modification of the protein; that is, there was a mass excess of approximately 3×162 (the mass excess of a single Amadori product). There are three lysine residues distributed within the primary sequence of human MIF, and since recombinantly-produced MIF protein begins with the second amino acid in the primary sequence, proline (because the normal initial vertebrate methionine residue is typically clipped off by the expressing bacteria), there is no free amino group associated with the amino-terminus of the protein. Taken together, this indicates that modification of side-chain amino groups of amino acids within the MIF peptide sequence can eliminate MIF D-dopachrome tautomerase activity. Thus, compounds that cause the modification of lysine residues of MIF are useful as inhibitors of MIF bioactivity, including, without limitation, the inflammatory and immunomodulatory activities of MIF.

What is claimed is:

1. A screening assay for compounds that inhibit the biological activity of MIF, comprising:

(a) preparing a reaction mixture of MIF and a MIF-substrate in the presence and absence of a test compound; and (b) detecting tautomerization of the MIF-substrate, in which a decrease in tautomerization of the MIF-substrate indicates the ability of the test compound to inhibit MIF activity.

2. The screening assay of claim 1 in which the MIF-substrate comprises D-dopachrome, D-dopachrome-methyl ester, or L-dopachrome-methyl ester.

3. The screening assay of claim 2 in which tautomerization of the MIF-substrate is detected colorimetrically or spectrophotometrically.

* * * * *